United States Patent
Ma et al.

(10) Patent No.: US 9,131,034 B2
(45) Date of Patent: *Sep. 8, 2015

(54) POWER MANAGEMENT FOR WIRELESS DEVICES

(71) Applicant: Abbott Medical Optics Inc., Santa Ana, CA (US)

(72) Inventors: Dung Ma, Anaheim, CA (US); James Gerg, Lake Forest, CA (US); Fred Lee, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/039,544

(22) Filed: Sep. 27, 2013

(65) Prior Publication Data

US 2014/0031091 A1 Jan. 30, 2014

Related U.S. Application Data

(63) Continuation of application No. 11/250,984, filed on Oct. 13, 2005, now Pat. No. 8,565,839.

(51) Int. Cl.
| | |
|---|---|
| *H04M 1/00* | (2006.01) |
| *H04B 1/38* | (2015.01) |
| *H02J 7/00* | (2006.01) |
| *A61B 17/00* | (2006.01) |
| *A61B 19/00* | (2006.01) |

(52) U.S. Cl.
CPC ............... *H04M 1/00* (2013.01); *H02J 7/0054* (2013.01); *A61B 2017/00212* (2013.01); *A61B 2017/00221* (2013.01); *A61B 2019/2269* (2013.01)

(58) Field of Classification Search
USPC ........ 455/572, 573, 574, 127.1, 127.2, 127.3, 455/127.4, 127.5, 343.1, 343.2, 343.3, 455/343.4, 343.5, 343.6; 307/46, 48, 49, 307/66; 320/149, 112, 106
See application file for complete search history.

(56) References Cited

U.S. PATENT DOCUMENTS

| | | |
|---|---|---|
| 1,848,024 A | 3/1932 | Owen |
| 3,076,904 A | 2/1963 | Claus et al. |
| 3,116,697 A | 1/1964 | Theodore |
| 3,439,680 A | 4/1969 | Thomas, Jr. |

(Continued)

FOREIGN PATENT DOCUMENTS

| | | |
|---|---|---|
| EP | 56019 A1 | 7/1982 |
| EP | 619993 A1 | 10/1994 |

(Continued)

OTHER PUBLICATIONS

Boyd, "Preparing for the Transition" in: The Art and the Science of Cataract Surgery, Chapter 7, 2001, pp. 93-133.

(Continued)

*Primary Examiner* — Ping Hsieh
(74) *Attorney, Agent, or Firm* — Abbott Medical Optics Inc.

(57) ABSTRACT

A method and apparatus for wireless device power management is provided. The method comprises providing a charge to an intermediate power cell by electrically connecting the intermediate power cell to a power source, disconnecting the intermediate power cell from the power source, and electrically connecting the wireless device to the intermediate power cell. Such electrical connecting enables power cell recharging within the wireless device.

18 Claims, 7 Drawing Sheets

(56) References Cited

U.S. PATENT DOCUMENTS

| | | | |
|---|---|---|---|
| 3,526,219 | A | 9/1970 | Lewis |
| 3,781,142 | A | 12/1973 | Zweig |
| 3,857,387 | A | 12/1974 | Shock |
| 4,037,491 | A | 7/1977 | Newbold |
| 4,189,286 | A | 2/1980 | Murry et al. |
| 4,193,004 | A | 3/1980 | Lobdell et al. |
| 4,564,342 | A | 1/1986 | Weber et al. |
| 4,590,934 | A | 5/1986 | Malis et al. |
| 4,665,621 | A | 5/1987 | Ackerman et al. |
| 4,706,687 | A | 11/1987 | Rogers et al. |
| 4,757,814 | A | 7/1988 | Wang et al. |
| 4,773,897 | A | 9/1988 | Scheller et al. |
| 4,837,857 | A | 6/1989 | Scheller et al. |
| 4,920,336 | A | 4/1990 | Meijer |
| 4,933,843 | A | 6/1990 | Scheller et al. |
| 4,954,960 | A | 9/1990 | Lo et al. |
| 4,965,417 | A | 10/1990 | Massie |
| 4,983,901 | A | 1/1991 | Lehmer |
| 4,998,972 | A | 3/1991 | Chin et al. |
| 5,006,110 | A | 4/1991 | Garrison et al. |
| 5,026,387 | A | 6/1991 | Thomas |
| 5,039,973 | A | 8/1991 | Carballo |
| 5,091,656 | A | 2/1992 | Gahn |
| 5,125,891 | A | 6/1992 | Hossain et al. |
| 5,160,317 | A | 11/1992 | Costin |
| 5,195,960 | A | 3/1993 | Hossain et al. |
| 5,195,961 | A | 3/1993 | Takahashi et al. |
| 5,195,971 | A | 3/1993 | Sirhan |
| 5,230,614 | A | 7/1993 | Zanger et al. |
| 5,249,121 | A | 9/1993 | Baum et al. |
| 5,268,624 | A | 12/1993 | Zanger |
| 5,271,379 | A | 12/1993 | Phan et al. |
| 5,282,787 | A | 2/1994 | Wortrich |
| 5,323,543 | A | 6/1994 | Steen et al. |
| 5,342,293 | A | 8/1994 | Zanger |
| 5,351,676 | A | 10/1994 | Putman |
| 5,454,783 | A | 10/1995 | Grieshaber et al. |
| 5,470,211 | A | 11/1995 | Knott et al. |
| 5,520,652 | A | 5/1996 | Peterson |
| 5,549,461 | A | 8/1996 | Newland |
| 5,554,894 | A | 9/1996 | Sepielli |
| 5,561,575 | A | 10/1996 | Eways |
| 5,580,347 | A | 12/1996 | Reimels |
| 5,591,127 | A | 1/1997 | Barwick, Jr. et al. |
| 5,657,000 | A | 8/1997 | Ellingboe |
| 5,676,530 | A | 10/1997 | Nazarifar |
| 5,676,650 | A | 10/1997 | Grieshaber et al. |
| 5,693,020 | A | 12/1997 | Rauh |
| 5,697,898 | A | 12/1997 | Devine |
| 5,700,240 | A | 12/1997 | Barwick, Jr. et al. |
| 5,733,256 | A | 3/1998 | Costin |
| 5,745,647 | A | 4/1998 | Krause |
| 5,747,824 | A | 5/1998 | Jung et al. |
| 5,777,602 | A | 7/1998 | Schaller et al. |
| 5,805,998 | A | 9/1998 | Kodama |
| 5,830,176 | A | 11/1998 | Mackool |
| 5,843,109 | A | 12/1998 | Mehta et al. |
| 5,879,298 | A | 3/1999 | Drobnitzky et al. |
| 5,883,615 | A | 3/1999 | Fago et al. |
| 5,899,674 | A | 5/1999 | Jung et al. |
| 5,928,257 | A | 7/1999 | Kablik et al. |
| 5,983,749 | A | 11/1999 | Holtorf |
| 6,002,484 | A | 12/1999 | Rozema et al. |
| 6,024,428 | A | 2/2000 | Uchikata |
| 6,062,829 | A | 5/2000 | Ognier |
| 6,077,285 | A | 6/2000 | Boukhny |
| 6,086,598 | A | 7/2000 | Appelbaum et al. |
| 6,117,126 | A | 9/2000 | Appelbaum et al. |
| 6,150,623 | A | 11/2000 | Chen |
| 6,179,829 | B1 | 1/2001 | Bisch et al. |
| 6,219,032 | B1 | 4/2001 | Rosenberg et al. |
| 6,251,113 | B1 | 6/2001 | Appelbaum et al. |
| 6,260,434 | B1 | 7/2001 | Holtorf |
| 6,360,630 | B2 | 3/2002 | Holtorf |
| 6,368,269 | B1 | 4/2002 | Lane |
| 6,411,062 | B1 | 6/2002 | Baranowski et al. |
| 6,424,124 | B2 * | 7/2002 | Ichihara et al. ............ 320/149 |
| 6,436,072 | B1 | 8/2002 | Kullas et al. |
| 6,452,120 | B1 | 9/2002 | Chen |
| 6,452,123 | B1 | 9/2002 | Chen |
| 6,491,661 | B1 | 12/2002 | Boukhny et al. |
| 6,511,454 | B1 | 1/2003 | Nakao et al. |
| 6,632,214 | B2 | 10/2003 | Morgan et al. |
| 6,674,030 | B2 | 1/2004 | Chen et al. |
| 6,830,555 | B2 | 12/2004 | Rockley et al. |
| 6,852,092 | B2 | 2/2005 | Kadziauskas et al. |
| 6,862,951 | B2 | 3/2005 | Peterson et al. |
| 6,962,488 | B2 | 11/2005 | Davis et al. |
| 6,962,581 | B2 | 11/2005 | Thoe |
| 7,012,203 | B2 | 3/2006 | Hanson et al. |
| 7,070,578 | B2 | 7/2006 | Leukanech et al. |
| 7,169,123 | B2 | 1/2007 | Kadziauskas et al. |
| 7,236,809 | B2 | 6/2007 | Fischedick et al. |
| 7,242,765 | B2 | 7/2007 | Hairston |
| 7,244,240 | B2 | 7/2007 | Nazarifar et al. |
| 7,289,825 | B2 | 10/2007 | Fors et al. |
| 7,300,264 | B2 | 11/2007 | Souza |
| 7,316,664 | B2 | 1/2008 | Kadziauskas et al. |
| 7,336,976 | B2 | 2/2008 | Ito |
| 7,381,917 | B2 | 6/2008 | Dacquay et al. |
| 7,439,463 | B2 | 10/2008 | Brenner et al. |
| 7,470,277 | B2 | 12/2008 | Finlay et al. |
| 7,883,521 | B2 | 2/2011 | Rockley et al. |
| 7,921,017 | B2 | 4/2011 | Claus et al. |
| 2001/0023331 | A1 | 9/2001 | Kanda et al. |
| 2001/0047166 | A1 | 11/2001 | Wuchinich |
| 2001/0051788 | A1 | 12/2001 | Paukovits et al. |
| 2002/0019215 | A1 | 2/2002 | Romans |
| 2002/0019607 | A1 | 2/2002 | Bui |
| 2002/0045887 | A1 | 4/2002 | DeHoogh et al. |
| 2002/0070840 | A1 | 6/2002 | Fischer et al. |
| 2002/0098859 | A1 * | 7/2002 | Murata ..................... 455/522 |
| 2002/0137007 | A1 | 9/2002 | Beerstecher |
| 2002/0179462 | A1 | 12/2002 | Silvers |
| 2003/0047434 | A1 | 3/2003 | Hanson et al. |
| 2003/0073980 | A1 | 4/2003 | Finlay et al. |
| 2003/0108429 | A1 | 6/2003 | Angelini et al. |
| 2003/0125717 | A1 | 7/2003 | Whitman |
| 2004/0037724 | A1 | 2/2004 | Haser et al. |
| 2004/0068300 | A1 | 4/2004 | Kadziauskas et al. |
| 2004/0092922 | A1 | 5/2004 | Kadziauskas et al. |
| 2004/0193182 | A1 | 9/2004 | Yaguchi et al. |
| 2004/0212344 | A1 * | 10/2004 | Tamura et al. ............ 320/114 |
| 2005/0054971 | A1 | 3/2005 | Steen et al. |
| 2005/0069419 | A1 | 3/2005 | Cull et al. |
| 2005/0070859 | A1 | 3/2005 | Cull et al. |
| 2005/0109595 | A1 | 5/2005 | Mezhinsky et al. |
| 2005/0118048 | A1 | 6/2005 | Traxinger |
| 2005/0130098 | A1 | 6/2005 | Warner |
| 2005/0209560 | A1 | 9/2005 | Boukhny et al. |
| 2005/0245888 | A1 | 11/2005 | Cull |
| 2005/0261628 | A1 | 11/2005 | Boukhny et al. |
| 2006/0036180 | A1 | 2/2006 | Boukhny et al. |
| 2006/0078448 | A1 | 4/2006 | Holden |
| 2006/0145540 | A1 | 7/2006 | Mezhinsky |
| 2006/0219049 | A1 | 10/2006 | Horvath et al. |
| 2006/0236242 | A1 | 10/2006 | Boukhny et al. |
| 2007/0016174 | A1 | 1/2007 | Millman et al. |
| 2007/0049898 | A1 | 3/2007 | Hopkins et al. |
| 2007/0060926 | A1 | 3/2007 | Escaf |
| 2007/0073214 | A1 | 3/2007 | Dacquay et al. |
| 2007/0073309 | A1 | 3/2007 | Kadziauskas et al. |
| 2007/0078379 | A1 | 4/2007 | Boukhny et al. |
| 2007/0249942 | A1 | 10/2007 | Salehi et al. |
| 2008/0033342 | A1 | 2/2008 | Staggs |
| 2008/0066542 | A1 | 3/2008 | Gao |
| 2008/0067046 | A1 | 3/2008 | Dacquay et al. |
| 2008/0112828 | A1 | 5/2008 | Muri et al. |
| 2008/0114289 | A1 | 5/2008 | Muri et al. |
| 2008/0114290 | A1 | 5/2008 | King et al. |
| 2008/0114291 | A1 | 5/2008 | Muri et al. |
| 2008/0114300 | A1 | 5/2008 | Muri et al. |
| 2008/0114311 | A1 | 5/2008 | Muri et al. |
| 2008/0114312 | A1 | 5/2008 | Muri et al. |

(56) References Cited

U.S. PATENT DOCUMENTS

| | | | |
|---|---|---|---|
| 2008/0114372 A1 | 5/2008 | Edwards et al. |
| 2008/0114387 A1 | 5/2008 | Hertweck et al. |
| 2008/0125697 A1 | 5/2008 | Gao |
| 2008/0125698 A1 | 5/2008 | Gerg et al. |
| 2008/0146989 A1 | 6/2008 | Zacharias |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2009/0005712 A1 | 1/2009 | Raney |
| 2009/0005789 A1 | 1/2009 | Charles |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |

FOREIGN PATENT DOCUMENTS

| | | | | |
|---|---|---|---|---|
| EP | 1010437 A1 | 6/2000 | | |
| EP | 1072285 A1 | 1/2001 | | |
| EP | 1113562 A1 | 7/2001 | | |
| EP | 1310267 A2 | 5/2003 | | |
| EP | 1550406 A2 | 7/2005 | | |
| EP | 1704839 A1 | 9/2006 | | |
| EP | 1787606 A1 | 5/2007 | | |
| EP | 1849443 A1 | 10/2007 | | |
| EP | 1849444 A1 | 10/2007 | | |
| EP | 1867349 A1 | 12/2007 | | |
| EP | 1873501 A1 | 1/2008 | | |
| EP | 1900347 A1 | 3/2008 | | |
| EP | 1925274 A2 | 5/2008 | | |
| ES | 2264369 A1 | 12/2006 | | |
| GB | 2230301 A | 10/1990 | | |
| GB | 2352887 A | 2/2001 | | |
| GB | 2352887 A | * | 2/2001 | ............... H02J 9/06 |
| JP | 2008188110 A | 8/2008 | | |
| WO | WO-9220310 A1 | 11/1992 | | |
| WO | WO-9317729 A1 | 9/1993 | | |
| WO | WO-9324082 A1 | 12/1993 | | |
| WO | WO-9632144 A1 | 10/1996 | | |
| WO | WO-9818507 A1 | 5/1998 | | |
| WO | WO-9917818 A1 | 4/1999 | | |
| WO | WO-0000096 A1 | 1/2000 | | |
| WO | WO-0070225 A1 | 11/2000 | | |
| WO | WO-0122696 A1 | 3/2001 | | |
| WO | WO-0234314 A1 | 5/2002 | | |
| WO | WO-2004096360 A1 | 11/2004 | | |
| WO | WO-2004114180 A1 | 12/2004 | | |
| WO | WO-2005084728 A2 | 9/2005 | | |
| WO | WO-2005092023 A2 | 10/2005 | | |
| WO | WO-2005092047 A2 | 10/2005 | | |
| WO | WO-2006101908 A2 | 9/2006 | | |
| WO | WO-2006125280 A1 | 11/2006 | | |
| WO | WO-2007121144 A1 | 10/2007 | | |
| WO | WO-2007143677 A2 | 12/2007 | | |
| WO | WO-2007143797 A1 | 12/2007 | | |
| WO | WO-2008030872 A1 | 3/2008 | | |
| WO | WO-2008060859 A1 | 5/2008 | | |
| WO | WO-2008060902 A1 | 5/2008 | | |
| WO | WO-2008060995 A1 | 5/2008 | | |
| WO | WO-2010054146 A1 | 5/2010 | | |
| WO | WO-2010054225 A2 | 5/2010 | | |

OTHER PUBLICATIONS

Definition of "Parameter", Retrieved from the Internet: < URL: http://dictionary.reference.com/browse/parameter>.

International Preliminary Report on Patentability and Written Opinion for Application No. PCT/US2006/39868, mailed on Apr. 16, 2008, 6 pages.

International Search Report for Application No. PCT/US07/083875, mailed on May 7, 2008, 4 pages.

International Search Report for Application No. PCT/US07/083880, mailed on May 30, 2008, 4 pages.

International Search Report for Application No. PCT/US07/084157, mailed on Apr. 1, 2008, 3 pages.

International Search Report for Application No. PCT/US07/084163, mailed on Apr. 1, 2008, 3 pages.

International Search Report for Application No. PCT/US08/064240, mailed on Oct. 29, 2008, 3 pages.

International Search Report for Application No. PCT/US08/071704, mailed on Nov. 26, 2008, 3 pages.

International Search Report for Application No. PCT/US08/072974, mailed on Feb. 23, 2009, 2 pages.

International Search Report for Application No. PCT/US2006/39868, mailed on Nov. 12, 2007, 3 pages.

International Search Report for Application No. PCT/US2009/052473, mailed on Nov. 2, 2009, 3 pages.

Phacoemulsification. Oct. 12, 2006. Wikipedia.com. Jun. 19, 2009 <http://en.wikipedia.org/wiki/Phacoemulsification>.

* cited by examiner

POWER MANAGEMENT FOR WIRELESS DEVICES

This application is a continuation application and claims priority to U.S. application Ser. No. 11/250,984 filed on Oct. 13, 2005, the entire contents of are hereby incorporated by reference in its entirety for all purposes as if fully set forth herein.

BACKGROUND OF THE INVENTION

1. Field of the Invention

The present invention relates generally to the field of medical systems, and more specifically to managing power for wireless devices.

2. Description of the Related Art

Current medical system product offerings typically transmit signals over a fixed wire or cable to connect removable or non-fixed subsystems and devices. Traditionally, these non-fixed wired subsystems and devices employ the same fixed wire connection to receive a constant reliable source of power. Examples of removable or non-fixed wired devices include monitors or monitoring equipment, test equipment, remote control devices, footpedals, and so forth.

The rapid advancement and proliferation of short-range radio technology now affords medical system product designers and manufacturers the ability to create and deploy non-fixed subsystems and devices without need for a conventional fixed physical communication cable. For example, non-fixed devices meeting or complying with the Institute of Electrical and Electronics Engineers (IEEE) 802.11g, IrDA (infrared data), and Ericsson Bluetooth™ specifications provide short-range radio technology to enable for wireless communications. These technologies enable the wireless transmission of signals over short distances between telephones, computers and other electronic devices. Bluetooth™ enabled devices are capable of an approximate 10-meter transmission range at data rates up to 720 kilobits/sec and provide better security features than devices implementing IEEE 802.11g communications.

However, the Bluetooth™ and IEEE 802.11g specifications only address the transmitting and receiving of communication and control signals. Non-fixed wireless medical subsystems and devices are typically without a fixed continuous reliable power source (i.e. wired alternating or direct current) and rely on internal batteries for operation when active. Due to the critical health support requirements for medical equipment and the potential catastrophic consequences of a power failure in such equipment, effective deployment of medical systems incorporating wireless devices require a highly reliable battery power management scheme to ensure a constant source of power to fielded non-fixed wireless subsystems and devices.

These active wireless medical devices, when used under normal operation, are exposed to numerous electrical safety and reliability issues. An example of safety issues include the wireless device and associated battery-charging mechanism (e.g. charging cradle or alternating current transformer) coming in contact with various caustic and corrosive chemicals and fluids in the operating theater. An example of reliability issues includes ensuring a battery health and status indication is available at all times to the user, such as a surgeon, thus ensuring consistent successful non-fixed wireless device operation.

Moreover, wireless medical subsystems and devices that use batteries as their power source are typically only available for a recharging cycle at the end of the surgery day when the device is not in operational use. At the end of the surgical day, medical systems and non-fixed wireless devices are typically moved and stored to the side of the operating room, frequently away from a source of electrical power. This poses a particular challenge for power management schemes, since operating room medical systems are unplugged from AC line power for storage at the end of the surgery day and power is not available for recharging the wireless subsystems and devices. Thus over a typical 24 hour operating day, the wireless device is in operation or available to the surgeon/user for a large part of the day and plugged into a base or recharger having no source of power. Reliable wireless device power management schemes in this environment must not only provide a reliable source of power but must also provide a mechanism for monitoring and reporting battery condition for wireless subsystems and devices, when an alternating current or direct current source is not available.

Thus it would be advantageous to offer an architecture and design that provides wireless battery operated subsystems and devices a reliable and highly available power management scheme to ensure safe and continuous peripheral product operation in an environment where the wireless device and base unit each have no source of power for extended periods of time.

SUMMARY OF THE INVENTION

According to one aspect of the present design, there is provided a method for managing power operating a wireless device. The method comprises providing a charge to an intermediate power cell by electrically connecting the intermediate power cell to a power source, disconnecting the intermediate power cell from the power source, and electrically connecting the wireless device to the intermediate power cell. The electrically connecting enables recharging of power cells within the wireless device.

Certain wired operation, wherein the wireless device is connected by wire to a base unit or intermediate power source, is also disclosed.

These and other advantages of the present invention will become apparent to those skilled in the art from the following detailed description of the invention and the accompanying drawings.

DESCRIPTION OF THE DRAWINGS

The present invention is illustrated by way of example, and not by way of limitation, in the figures of the accompanying drawings in which.

DETAILED DESCRIPTION OF THE INVENTION

The present design provides a method and apparatus for managing power associated with non-fixed battery operated wireless devices. A power management arrangement or subsystem may provide a mechanism for monitoring and reporting the health and status of a battery used to power wireless devices, particularly in instances where the wireless device or devices operate in a medical theater, including but not limited to an operating room. The power management subsystem may include a novel in-situ battery recharging arrangement. The present design is directed to managing power in a wireless, rechargeable device, typically employed in a medical scenario but applicable in other scenarios, where power management includes recharging the monitoring health/status of one or more batteries, reporting health/status of the battery or batteries, indicating current battery condition to a user, and alerting the user when necessary to recharge the batteries.

While the present design may be used in various environments and applications, it will be discussed herein with a particular emphasis on a medical or hospital environment, where a surgeon or health care practitioner performs, for example, a phacoemulsification technique to effect a cataract procedure using a medical system that incorporates a battery powered wireless device, such as a switch (such as a footswitch or footpedal), to control the medical system.

The term "wireless device" or non-fixed wireless device" or the like as used herein means a device capable of receiving and/or transmitting information wirelessly, i.e. over or through the air, and not the fact that the device may be disconnected from a power source, which may be true but is not absolutely necessary in all circumstances.

The present design provides an arrangement that enables users of battery operated wireless medical devices to monitor battery condition, including but not limited to remaining useful charge duration. This arrangement provides monitoring and reporting information services in regard to the wireless medical device battery condition, including providing an alert when necessary to recharge the battery to ensure continuous, reliable, and safe use.

Figure 1:
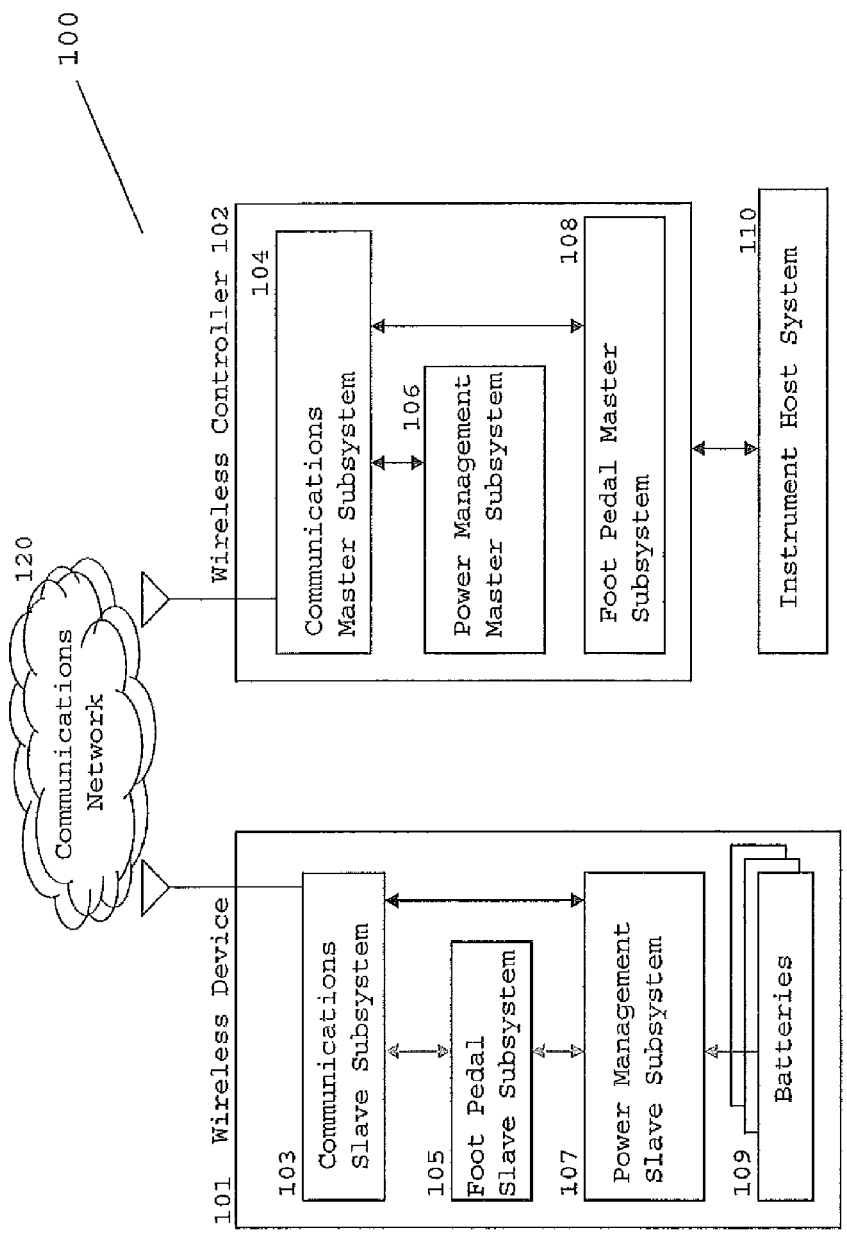
FIG. 1 is a block diagram illustrating the present design components and interfaces of a wireless medical system with a battery power management subsystem.

FIG. 1 illustrates the present design components and interfaces of a medical system 100, where the particular embodiment illustrated in FIG. 1 contemplates that the wireless or remote device is a footpedal. The medical system 100 in this embodiment includes a wireless device 101, a wireless controller 102, and an instrument host system 110. The wireless device 101 obtains power for operation from one or more batteries 109. A power management slave subsystem 107 may observe the health and status of each battery 109 installed in the wireless device. Observing the health and status may include measuring battery reserve to determine current battery condition and reporting the measured result to a communication slave subsystem 103 within the wireless device 101. The communication slave subsystem 103, embedded within the wireless device 101, may access the communication network 120 to transmit the observed health and status information received from the power management slave system 107. Moreover, the communication slave subsystem 103 may access the communication network 120 to transmit footpedal slave subsystem 105 data relating, but not limited to, footpedal position and other footpedal parameters received from the footpedal slave system 105. The wireless device 101 may report observed health and status and other power management information through a communications network 120 to the wireless controller 102.

The communications network 120 may employ any network communications protocol sufficient for serving the purposes of communications network 120. Additionally, the term "communications network" or "communications system" as used herein is used in its most expansive sense and applies to any communications system through which any information may be transferred to and from a wireless device, and includes, without limitation, transmission by static, active, dynamic communications protocols or otherwise. While the present design may use various communication protocols, such as IrDA, Bluetooth™, 802.11g, or other protocol, it will be discussed herein implementing and complying with Ericsson's Bluetooth™ protocol specification.

From communication network 120, the wireless controller 102 receives wireless device 101 transmissions via a communication master subsystem 104, typically comprising a transmitter and receiver operating, for example, using the wireless 802.11(g) or Bluetooth™ protocols. The communications master subsystem 104 receives and forwards information to the power management master subsystem 106 for further processing, wherein the information may include but is not limited to existing battery power. Furthermore, the communications master subsystem 104 receives and forwards information, including but not limited to information such as footpedal position and state parameters, to the footpedal master subsystem 108 for additional processing.

The present design monitors and reports one or more power management parameters observed by the power management slave subsystem 107. Power management parameters may include but are not limited to, battery levels indicating overall current remaining. In addition, footpedal status changes, such as footpedal switches remaining inactive for a period of time, may be observed and reported by the footpedal slave subsystem 105 to the power management slave subsystem 107.

The power management scheme may invoke a reduced level of communications, or other power saving mechanisms, during inactive periods to reduce battery consumption. Reduced communications may include not transmitting/receiving as frequently as normal, while power reduction modes may include reducing power during periods when minimal operation occurs, or turning off the unit until commanded to be on by the user. Other reduced power management schemes may be employed. Furthermore, the power management slave subsystem 107 may generate either a visible or audible indication, or any combination thereof, for example illuminating a light emitting diode (LED) and periodically sounding an audible tone, to indicate sufficient battery power is available. Moreover, the present design may provide an alternate blinking LED or change in frequency or duration of the audible tone, or any combination thereof, to indicate when the battery power falls below a certain threshold (e.g. less than a certain voltage). In addition, the footpedal management slave subsystem 107 may provide constant illumination of one or more LEDs, provide blinking illumination of one or more LEDs, and use one or more colored LEDs to indicate battery charging modes. Battery charging modes may include, but are not limited to, a trickle charge mode and a fast charge mode.

The footpedal master subsystem 108 may communicate with an instrument host system 110 using a fixed signaling and control cable. The instrument host system 110 may be connected to the wireless controller 102. The wireless controller may provide footpedal switch position and rate of position change, including but not limited to, pitch and yaw quantities to the instrument host system 110.

The present design may operate in three different modes (i.e. configurations). A charging mode, wired operational mode, and wireless operational mode may be provided to enable charging of the wireless device, particularly in circumstances where the base unit or wireless controller 102 is not connected to a source of AC power for an extended period of time, such as overnight. The charging mode typically occurs at the end of the surgical day, when the wireless device 101 is not in operational use (i.e. out-of-service) and is stored in the charging cradle. The wired operational mode employs a fixed cable to provide signal and power between the wireless device 101 and the wireless controller 102 when in service. The wireless operational mode employs an internal battery 109 for power and receives signals across a communications network 120 enabling the same degree of facility as the in-service wired mode provides.

Figure 2B:
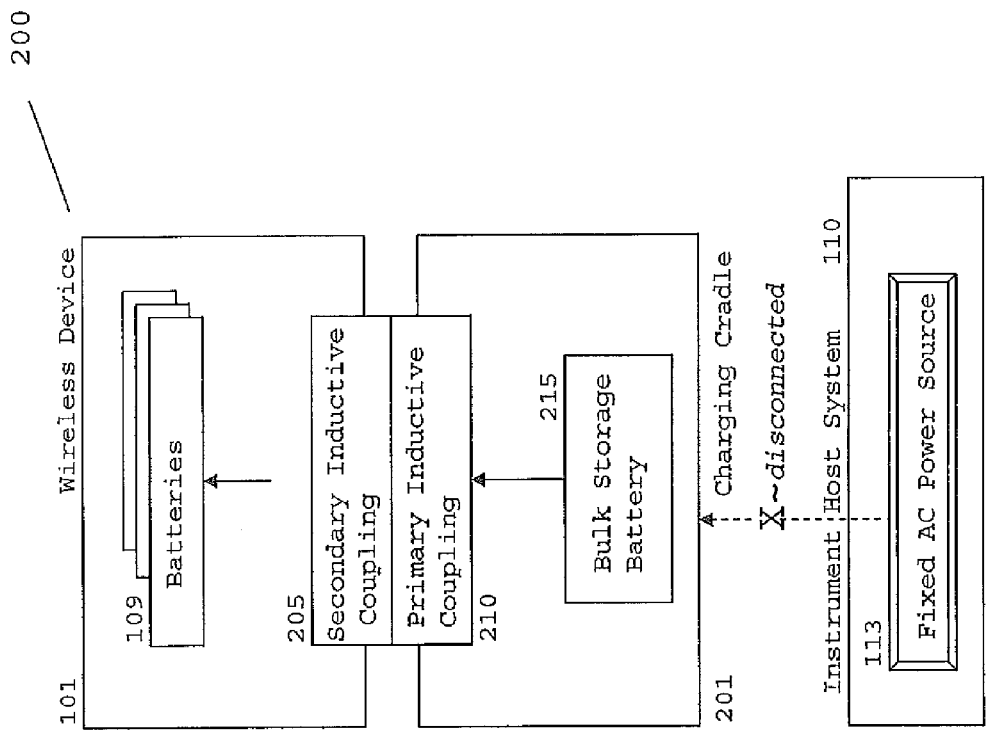
FIG. 2B is a block diagram illustrating the present design components and interfaces of a wireless device being recharged in a charging cradle.
Figure 2A:
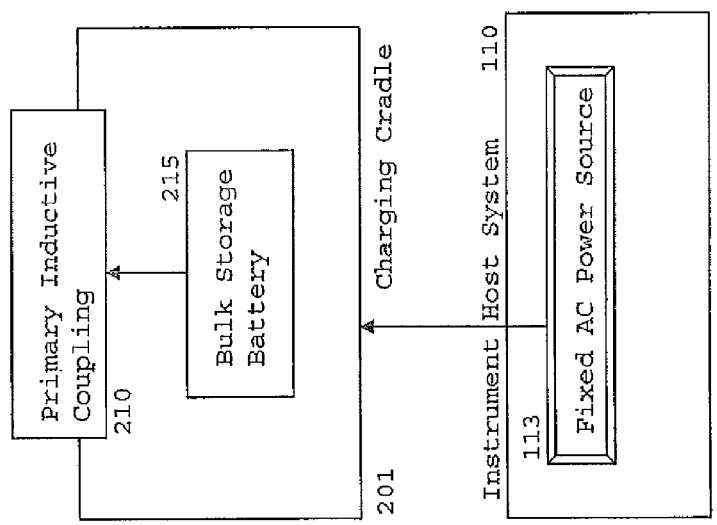
FIG. 2A is a block diagram illustrating the present design components and interfaces of a charging cradle.

FIG. 2A illustrates (with further reference to FIG. 1) components of the present design and interfaces of a charging cradle 201. The wireless device 101 may be removed from the charging cradle 201 during the day for use in surgical procedures. When the wireless device 101 is removed from the charging cradle 201 and a fixed AC power source 113 is available (e.g. supplied by the host system 110), the charging cradle 201 provides DC current to charge an internal secondary power source, such as a battery, capacitor, or other chargeable device. At the end of the surgical day, the wireless peripheral, such as a wireless footpedal, can be returned to the charging cradle 201. However, at the end of the surgical day, the fixed alternating current power source 113 may be disconnected, as shown in FIG. 2B.

While the present design may use various internal secondary power sources, the embodiment discussed herein comprises use of a bulk storage battery 215. FIG. 2B illustrates the present design components and interfaces for a wireless device 101 being recharged in a charging cradle 201 at the end of the surgical day, where power has been removed from the charging cradle 201. The present design operates to recharge one or more internal batteries 109 of a wireless device 101 using the charging cradle 201. Moreover, the charging cradle 201 may be used to recharge the batteries 109 within one or more wireless devices 101 by simply placing the device into the cradle.

During the surgical day, operating room personnel connect the medical system 100 to alternating current line power. The charging cradle 201, built into the host system 110, receives power from the medical system 100 and charges an internal bulk storage battery 215.

At the end of each surgical day, the wireless device 101 is cleaned by operating room personnel and returned to the built-in charging cradle 201 for storage. Operating room personnel may then move the medical system 100 to the side of the operating room, out of the way, and disconnect alternating current line power (i.e. unplug for safe storage).

A primary and secondary magnetic inductive coupling mechanism provides a transfer of charge from the bulk storage battery 215, located within the charging cradle 201, to the wireless device 101.

The wireless device 101 may provide a mating half of a magnetic inductive coupling 205 mechanism that receives power from the bulk storage battery 215 within the charging cradle 201. The charging cradle 201 provides a primary half of a magnetic inductive coupling 210 mechanism, that when joined with the wireless device 101 secondary inductive coupling 205 enables current to flow from the bulk storage battery 215 to the wireless device 101 secondary inductive coupling 205 that in turn supplies this current to the batteries 109 sufficient for recharging said batteries.

Other transfer mechanisms may be employed to transfer current from the bulk storage battery, such as transformers, transducers, noninductive circuitry, or other appropriate charge transfer devices. The net result and desired functionality is the ability to transfer current from the storage battery 215 to the wireless device 101.

The foregoing design enables the wireless device 101 to be removed from the charging cradle 201 during the day and used in normal operation. In the embodiment illustrated, the wireless device 101 may be a footpedal, but another removable device may be employed using this charging arrangement or subsystem, including devices not in communication with the host system 110. While used, the battery power of the wireless device will likely decrease and may fall below a threshold. At the same time, namely during the day in an operating environment while the wireless device 101 is being used, bulk storage battery 215 may be charging using, for example, AC current via a conventional wall socket, fixed power source, or other appropriate power source. At the end of the day, the wireless device 101 is replaced in the charging cradle 201, and the charging cradle 201 may be disconnected from the power source due to the need to store medical equipment in a particular manner. At this point, the bulk storage battery will have full charge and be able to charge the wireless device 101 without the presence of the power source.

Figure 3:
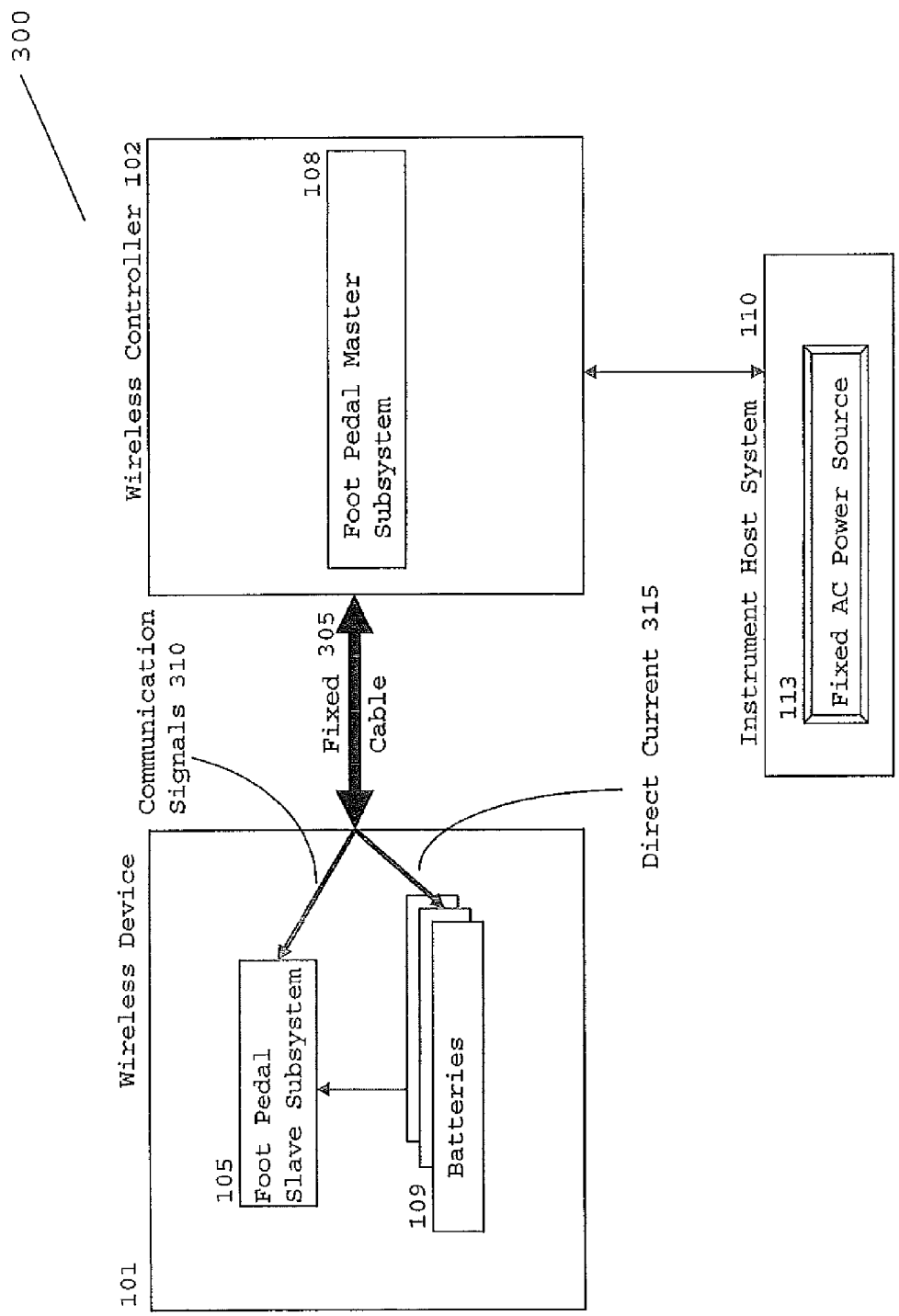
FIG. 3 is a block diagram illustrating the present design components and interfaces of a wireless device operating in a wired mode.

FIG. 3 illustrates the present design components with the interfaces of a wireless device operating in a wired mode. In the wired mode, a fixed physical cable 305 connects the wireless device 101 to the wireless controller 102. The fixed cable 305 supplies both communication signals 310 and direct current 315 between the wireless controller 102 and wireless device 101. In the wired configuration, the batteries 109 may be recharged by receiving current from the host instrument 110 during a surgical procedure in concert with the exchange of communication signals 310. In the embodiment illustrated, the footpedal master subsystem 108 receives these communication signals 310 and provides these signals to the instrument host system 110. Communication signals may include but are not limited to position of a footpedal, such as pitch and yaw positions, button pushes or "stomp" values, or other appropriate states in the case of a footpedal. Communication signals in other equipment, such as monitoring devices or test equipment, may include data or state values applicable to the device employed.

Figure 4:
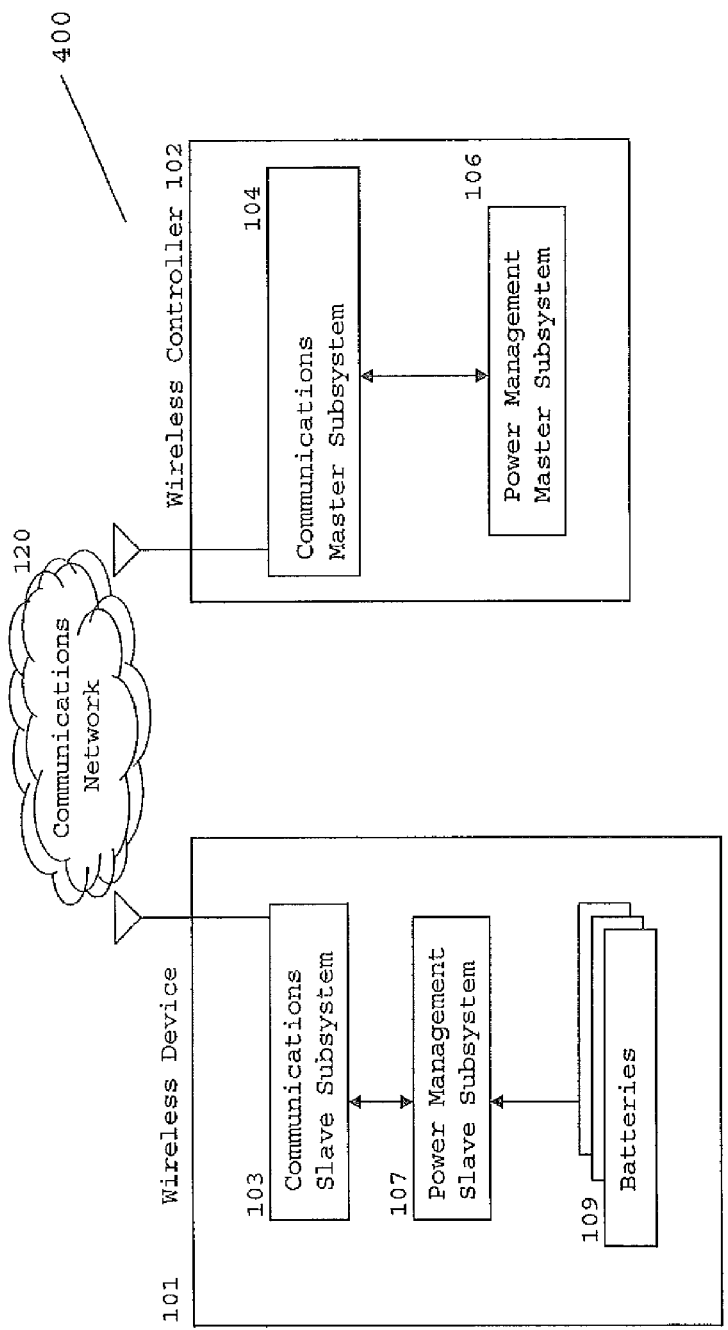
FIG. 4 is a block diagram illustrating the present design components and interfaces of a wireless device operating in a wireless mode.

FIG. 4 illustrates the present design components and interfaces of a wireless device 101 operating in a wireless mode. In the wireless mode, a communications network 120 replaces the fixed cable found in the wired mode to enable exchange of communication signals 310 between the wireless device 101 and the wireless controller 102. In the wireless mode, the wireless device 101 receives power from internal batteries 109. In this configuration, the health and status of one or more batteries 109 may be monitored and reported by the power management slave subsystem 107, either to the user or to the instrument host system (not shown in this view). The wireless controller 102 searches for a unique wireless device 101 using, for example, Bluetooth™ short-range radio techniques. Searching is complete when the correct wireless device 101 is located. At this point, the wireless controller 102 'pairs-up' or 'matches' with the unique wireless device 101 to enable communication of power management and other device information, such as signal and control. The specific techniques and details associated with Bluetooth™ searching and pairing mechanism are generally known to those skilled in the art. Other protocols, including but not limited to IrDA and IEEE 802.11g, may search and connect to other devices. For example, IEEE 802.11g may employ link control procedures known to those skilled in the art and specified by the standard, while a protocol such as IrDa may employ optical locating and searching techniques again known to those skilled in the art. The power management master subsystem 106 may prompt the power management slave subsystem 107 to acquire battery 109 health and status information, such as the charge remaining.

Figure 5A:
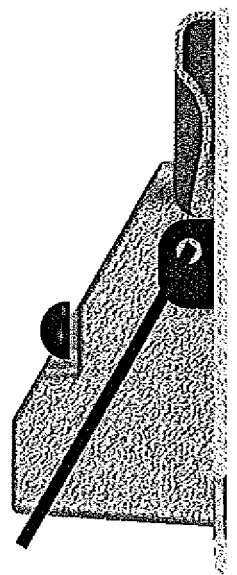
FIG. 5A shows an isometric view and a side view of a footpedal that may be employed in accordance with the current design.
Figure 5A:
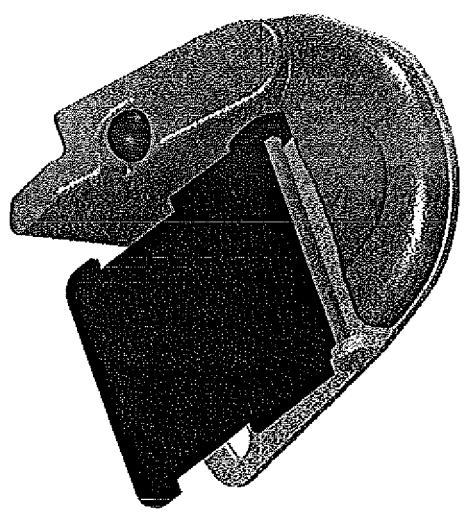
Figure 5B:
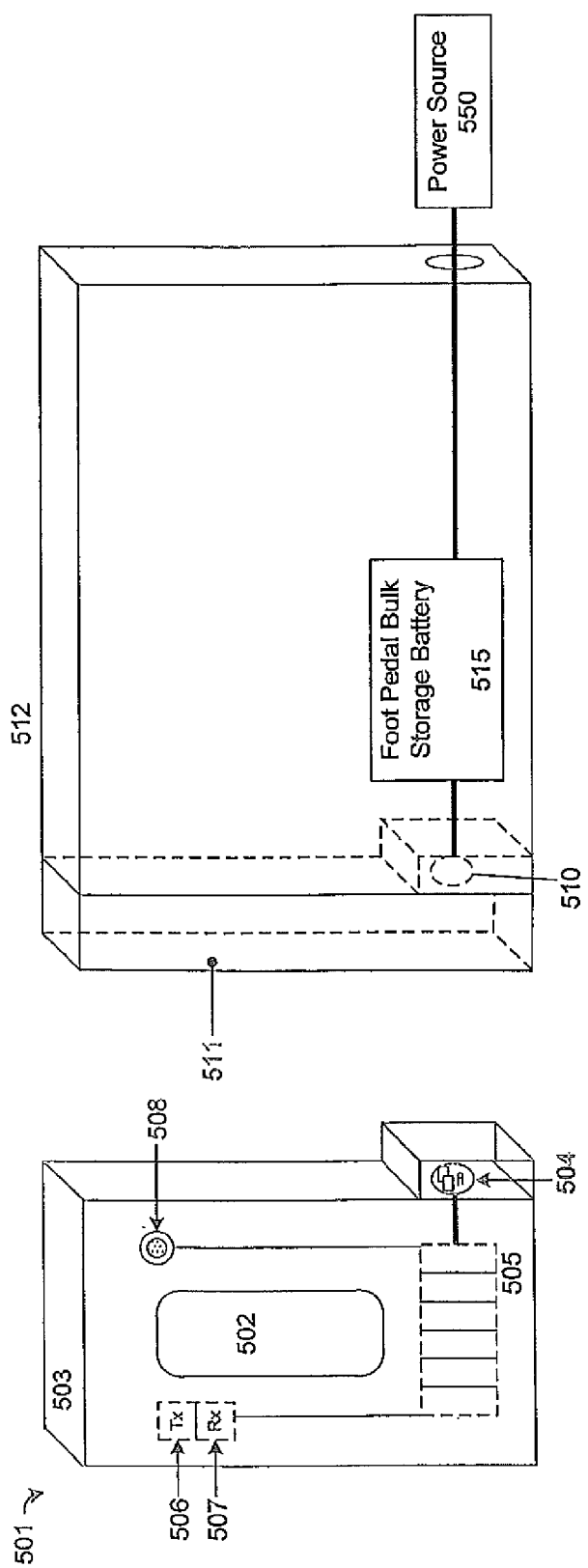
FIG. 5B is a conceptual illustration of the footpedal embodiment and associated base station and power source components.

FIG. 5A illustrates an isometric and side view of a footpedal usable in accordance with the present design. FIG. 5B shows the conceptual connections between the footpedal 501 and the base unit and power source. Footpedal 501 includes pedal 502, base 503, and electrical interface 504 here shown at the side of the base 503. The footpedal 501 in this view includes batteries 505, typically rechargeable batteries, connected to the electrical interface. A transmitter 506 and receiver 507 are provided in the footpedal 501 in this embodiment, and in this embodiment a "charge LED" 508 is provided that is constantly on when the remaining battery charge in the wireless device is above a certain threshold, such as, for example, 10 percent of total potentially available charge. When the amount of battery charge is below 10 percent, charge LED 508 blinks on and off, warning the user that power is low and the unit should be recharged.

Figure 6:
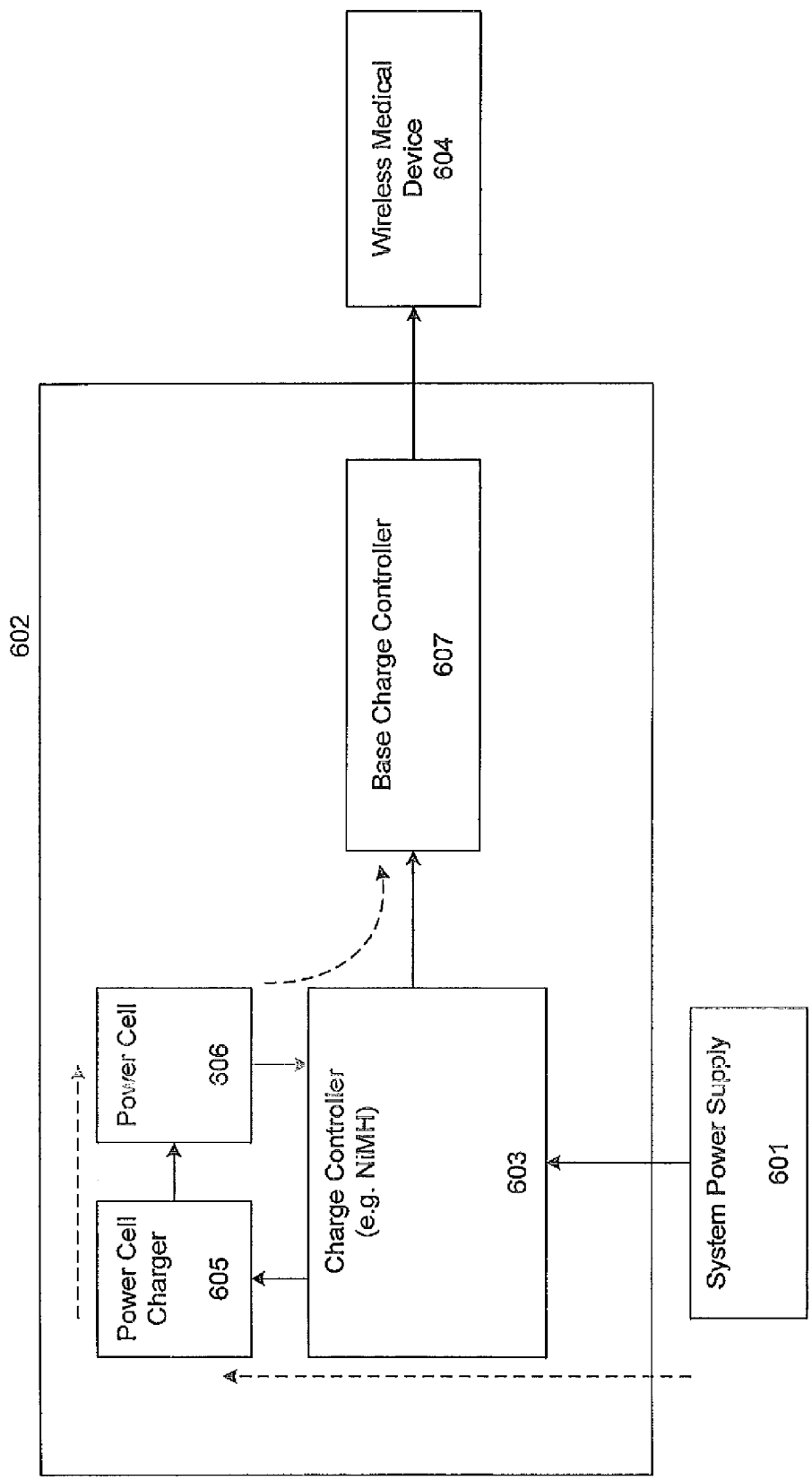
FIG. 6 illustrates an alternate embodiment of the present design.

The footpedal 501 fits into the footpedal charging cradle 511, such as at the end of the day, where the footpedal charging cradle 511 in this embodiment is formed within the base unit or footpedal host system 512. The electrical interface 504 of footpedal 501 in this embodiment may be matched or joined to the electrical interface 510 of charging cradle 511, and once joined, the batteries 505 may be charged. As may be appreciated, the electrical interface 504 may take varying forms, including but not limited to a standard three prong plug input, and the charging cradle 511 physical interface with footpedal 501 may take different forms, such as a receptacle receiving an insert, or a tab and slot arrangement. The base unit or footpedal host system 512 may include footpedal bulk storage battery 515. As described, footpedal bulk storage battery 515 may be charged when the footpedal 501 is operating remotely and electrically disconnected from the footpedal charging cradle 511. When the footpedal 501 is properly inserted into the footpedal charging cradle 511 at the end of the day, the footpedal 501 is recharged by the bulk storage battery if the power source 550 is removed. The footpedal 501 is recharged by the Power Source 550 if it is connected. Footpedal bulk storage battery 515 may be connected to or disconnected from power source 550. FIG. 6 shows an alternate version of the present design. From FIG. 6, system power supply 601 provides power to base unit 602. As noted, system power supply 601 may be any type of fixed or non fixed power source, including but not limited to a standard wall socket or a power cell or battery source. Charge controller 603 receives power and may either supply power to the base charge controller 607 or to the power cell charger 605. Power cell 606, as shown contained within base unit 602, may be charged by power cell charger 605. One embodiment of the power cell 606, also called an intermediate or secondary power cell or source, is a 12 volt battery.

In "charging" mode, power flows from the system power supply 601 to the charge controller 603 to power cell charger 605 and ultimately power cell 606. Indication may be provided from the power cell 606 to the charge controller 603 in the form of an amount already charged or needing to be charged, such as in a percentage form.

In one embodiment, the power cell 606 may provide an indication that it is 20 percent charged, 80 percent charged, and so forth. Once the power cell charge exceeds a certain threshold, as judged by the charge controller 603, the charge controller may cease supplying power to the power cell charger 605 and power cell 606. Operation may then turn to a "recharging" or a "power supply" mode. Recharging is caused by the charge controller 603 enabling power to pass from power cell 606 either through the charge controller 603 as shown or directly to the base charge controller 607. Charge may then be provided from base charge controller 607 of the base unit 602 to wireless medical device 604, thereby recharging the device even in circumstances where the base unit 602 is disconnected from power supply 601. While base charge controller 607 is illustrated as a component or module separate from charge controller 603, the two units may be combined into a single unit demonstrating the functionality described herein for base charge controller 607 and charge controller 603. Further, the functionality discussed with respect to base charge controller 607 and charge controller 603 and the various modules of FIG. 6 and the other figures presented may be combined, employed in different modules, or omitted where desired.

If the wireless medical device 604 is operating and connected via wired connection, such as a cable, to the base unit 602 while base unit 602 is connected to power supply 601, charging of power cell 606 is through power cell charger 605 and recharging of wireless medical device is through system power 601. The result is the ability to operate the wireless device relatively indefinitely by periodically recharging batteries or power cells within the wireless device. The connection between wireless medical device 604 and base unit 602 may be a cable or other electrical connection such as a plug and socket.

The foregoing is not determinative or exclusive or inclusive of all components, interfaces, communications, and operational modes employable within the present design. The design presented herein and the specific aspects illustrated are meant not to be limiting, but may include alternate components while still incorporating the teachings and benefits of the invention, namely a wireless device power management apparatus employing a wireless medical device, wireless controller, a communications network, and instrument host system to facilitate surgeons while performing procedures. While the invention has thus been described in connection with specific embodiments thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for supplying power to a wireless medical device, comprising:
   determining the operating mode of the wireless medical device, wherein the operating mode of the medical device includes a charging mode, a wired operation mode and a wireless operation mode;
   selecting, based upon the determined operating mode, the source of direct current power for the wireless medical device,
   wherein the selected source of direct current power for the wireless medical device is a physical cable from a base unit if the wireless medical device is in the wired operation mode,
   wherein the selected source of direct current power for the wireless medical device is one or more power cells contained in the wireless medical device if the medical device is in the wireless operation mode;
supplying the selected source of the direct current power to the wireless medical device; and
charging, based upon the determined operating mode of the wireless medical device, one or more power cells,
wherein the one or more power cells contained in the wireless medical device are charged if the wireless medical device is in the charging mode,
wherein the one or more power cells comprise a secondary power source contained within a second base unit and are charged if the wireless medical device is in the wired operation mode or the wireless operation mode.

2. The method of claim 1, wherein the charging further comprises recharging one or more wireless medical device power cells using the secondary power source when the wireless medical device is in direct contact with the second base unit.

3. The method of claim 1, wherein the charging further comprises recharging the one or more power cells in the wireless medical device when a fixed alternating current power source is unavailable.

4. The method of claim 1, wherein the charging further comprises an inductive coupling to transfer energy from the secondary power source to the one or more power cells in the wireless medical device.

5. The method of claim 1, wherein the selected source of direct current power is a fixed cable providing direct current to the wireless medical device from a fixed external alternating current line power source if the wireless medical device is in the wired operation mode.

6. The method of claim 1, wherein supplying further comprises providing direct current to the one or more power cells of the wireless medical device for the purposes of recharging the one or more power cells.

7. The method of claim 1, wherein the charging further comprises:
providing a charge to a secondary power source by electrical connection to direct current;
disconnecting the secondary power source from the direct current; and
electrically connecting the wireless medical device to the secondary power source, wherein the step of electrically connecting enables recharging of the one or more power cells.

8. The method of claim 7, further comprising:
monitoring the status of at least one of the one or more power cells contained in the wireless medical device;
reporting a status of the one or more power cells, said reporting indicating a current condition of the one or more power cells; and
alerting a user when advisable to recharge the one or more power cells in the wireless medical device.

9. The method of claim 8, wherein reporting comprises providing at least one of a visible signal and an audible signal informing a user of power cell status.

10. The method of claim 8, wherein reporting comprises providing at least one of a visible signal and an audible signal informing a user that power cells require recharging.

11. The method of claim 7, wherein providing the charge to the secondary power source comprises controlling current to flow from the connection to direct current through a controller to the secondary power source.

12. The method of claim 7, wherein the step of electrically connecting the wireless medical device to the secondary power source enables inductive transfer of current using a charge controller to the wireless medical device.

13. The method of claim 1, wherein the second base unit further comprises a charging cradle, and the wireless medical device is fitted within the charging cradle to recharge the one or more power cells.

14. The method of claim 13, wherein said charging cradle further comprises a primary inductive coupler and a fixed alternating current power source.

15. The method of claim 14, wherein said communications network employs a wireless communications protocol and the method includes transmitting a plurality of observed power management parameters between the wireless medical device and the base unit.

16. The method of any of claim 13, wherein the base unit further comprises a communications network, and the method includes transmitting information by a transmitter in the wireless medical device and receiving the information by the communications network.

17. The method of claim 16, wherein said charging cradle further comprises a primary inductive coupler and a fixed alternating current power source.

18. The method of claim 1, wherein the base unit is an intermediate power source.

* * * * *